(12) United States Patent
Seiferlein et al.

(10) Patent No.: US 8,092,421 B2
(45) Date of Patent: Jan. 10, 2012

(54) DUAL-CHAMBER CARPULE

(75) Inventors: Werner Seiferlein, Frankfurt am Main (DE); Jörn Möckel, Frankfurt am Main (DE); Martin Zink, Frankfurt am Main (DE)

(73) Assignee: Sanofi-Aventis Deutschland GmbH (DE)

( * ) Notice: Subject to any disclaimer, the term of this patent is extended or adjusted under 35 U.S.C. 154(b) by 0 days.

(21) Appl. No.: 12/636,948

(22) Filed: Dec. 14, 2009

(65) Prior Publication Data
US 2010/0262074 A1  Oct. 14, 2010

Related U.S. Application Data (63) Continuation of application No. PCT/EP2008/004356, filed on May 31, 2008.

(30) Foreign Application Priority Data

Jun. 14, 2007  (EP) ..................... 07011686

(51) Int. Cl.
*A61M 5/19* (2006.01)
(52) U.S. Cl. ...................................... 604/89
(58) Field of Classification Search .............. 604/82, 604/89, 90, 91
See application file for complete search history.

(56) References Cited

U.S. PATENT DOCUMENTS

| | | | |
|---|---|---|---|
| 4,254,768 A | | 3/1981 | Ty |
| 5,069,670 A | * | 12/1991 | Vetter et al. .............. 604/243 |
| 5,788,670 A | | 8/1998 | Reinhard et al. |
| 6,349,850 B1 | | 2/2002 | Cheikh et al. |
| 6,544,233 B1 | * | 4/2003 | Fukui et al. .............. 604/191 |
| 6,645,179 B1 | * | 11/2003 | Ishikawa et al. .......... 604/181 |
| 2003/0036724 A1 | * | 2/2003 | Vetter et al. ............... 604/85 |
| 2006/0173409 A1 | | 8/2006 | Yang |

FOREIGN PATENT DOCUMENTS

| | | |
|---|---|---|
| DE | 4445969 | 3/1996 |
| EP | 0520618 | 12/1992 |
| EP | 0743072 | 11/1996 |
| GB | 2010681 | 7/1979 |

* cited by examiner

*Primary Examiner* — Nicholas Lucchesi
*Assistant Examiner* — Aarti B Berdichevsky
(74) *Attorney, Agent, or Firm* — McDonnell Boehnen Hulbert & Berghoff LLP (57) ABSTRACT

The invention relates to a dual-chamber carpule having (1) a first partial cylinder comprising a sealing cap, a bypass, and an intermediate stopper, (2), an optional sealing element, and (3) a second partial cylinder comprising an end stopper and, optionally, a stop, an axial groove, and an additional intermediate stopper; the invention further relates to a method for producing and filling said dual-chamber carpule.

14 Claims, 5 Drawing Sheets

DUAL-CHAMBER CARPULE

This application is a continuation of International application No. PCT/EP2008/004,356, filed May 31, 2008, which is incorporated herein by reference in its entirety; which claims the benefit of priority of European Patent Application No. 07011686.8, filed Jun. 14, 2007.

Two-chamber carpules are used in medicine for administering preparations that comprise two components. There are two possibilities here for combining the components, namely the liquid/liquid combination and the solid/liquid combination.

Two-chamber carpules have the advantage that the mixing of the two components can take place without decanting into another container and that administering can then be performed directly from the container. Two-chamber carpules can be used in reusable syringe or pen systems intended for them.

DE 4445969, EP 718002 and U.S. Pat. No. 5,778,670 describe syringe cylinders of two-chamber syringes for two components to be applied, a first part-cylinder, preferably the part-cylinder on the head side, containing a medicament to be lyophilized, and a second part-cylinder, preferably the part-cylinder on the plunger side, containing a liquid component. During administering, the powdered medicament mixes with the liquid component by way of a bypass. The part-cylinder on the needle side contains the bypass and is closed at the proximal end by a plug. The part-cylinder on the plunger side is closed at the proximal end on the plunger side (FIG. 2) by a plug and optionally at the distal end (FIG. 3) by a further plug. The two part-cylinders are connected to each other by means of material bonding (by welding) or by means of nonpositive engagement (by adhesion). The syringe cylinders described have a bypass, which is preferably formed in such a way that it does not increase the diameter of the syringe cylinder. The material of the front part-cylinder is preferably plastic. In the method for filling the syringe cylinder, the syringe head of the first part-cylinder is closed by a so-called tip cap, i.e. by a loose closure through which the surrounding vacuum can be passed on to the interior of the syringe cylinder in the freeze-drying that follows filling with a lyophilizate, and which is only securely closed after the freeze-drying step. Separate filling into a first part-cylinder and a second part-cylinder avoids cross contamination and permits optimum utilization of the process space of the lyophilizer.

European patent application EP 520618 describes a prefilled syringe comprising two part-cylinders, the first part-cylinder, preferably the part-cylinder on the head side, which comprises the needle or the outlet, containing a lyophilized, powdered medicament, and the second part-cylinder, preferably the part-cylinder on the plunger side, containing a second, liquid component. During administering, the powdered medicament mixes with the liquid component by way of a bypass. The part-cylinder on the needle side contains the bypass and is closed at the proximal end by a plug. The part-cylinder on the plunger side is closed at the distal end and at the proximal end by a plug in each case. The two part-cylinders are separately sealed by means of the plugs and connected to each other by means of flanges, the proximal plug of the part-cylinder on the head side and the distal plug of the part-cylinder on the plunger side being positively connected to each other after being joined together, and the overall length of the two plugs being shorter than the length of the bypass.

GB 2010681 describes a two-chamber syringe for administering a liquid comprising two part-cylinders, the first part-cylinder being formed as a needle holder and comprising a channel to the outlet, and the second part-cylinder, on the plunger side, containing liquid. The first part-cylinder does not contain any substance to be administered. During administering, a plunger with which the part-cylinder on the plunger side is closed at the distal end is moved in the direction of the syringe head, whereby the liquid can be applied by way of the channel of the first part-cylinder.

FR 1099362 describes a two-chamber syringe comprising two part-cylinders, the first part-cylinder, on the head side, containing a sterile powder or a sterile liquid and the second part-cylinder, on the plunger side, containing a liquid. During administering, the sterile powder or the sterile liquid of the first part-cylinder mixes with the liquid of the second part-and cylinder by way of a bypass in the first part-cylinder, on the needle side. The part-cylinder on the plunger side is closed at the distal end by a plug and at the proximal end by a plunger. The two part-cylinders are connected to each other by adhesion or welding by means of flanges or by means of a further (over)cylinder, the inside diameter of which corresponds to the outside diameter of the two part-cylinders.

The prior-art syringe systems have the disadvantage that they are not suitable for insertion into an application system (for example into a pen system) and/or the solid component first has to be lyophilized in the part-cylinder on the needle side in order to obtain a solid, powdered component. Moreover, no solution compensating for the pressure produced when the two part-cylinders are joined together is mentioned in the prior art.

The object of the present invention is therefore to provide an improved and more cost-effective method for producing two-chamber carpules and for filling two-chamber carpules.

The present invention relates to a two-chamber carpule comprising
a) a first part-cylinder (1) on the head side, which forms a chamber, containing
 a bypass (3),
 an opening for receiving an intermediate plug (6) at the proximal end (4),
 and an intermediate plug (6) in the opening of the proximal end,
b) a liquid- and gas-tight closure (5) at the end on the head side of the first part-cylinder (1) on the head side,
c) a second part-cylinder (2) on the head side, which forms a second portion of the two-chamber carpule assigned to the second chamber, containing
 an opening at the distal end (8),
 an opening (9) for receiving an end plug (10) at the end on the plunger side, and
 an end plug (10) in the opening of the end on the plunger side of the second part-cylinder,
 optionally a second intermediate plug (17) at the distal end,
d) optionally a sealing element (7) between the first part-cylinder and the second part-cylinder.

The proximal end of the first part-cylinder and the distal end of the second part-cylinder are connected to each other in a sealed manner.

The invention also relates to the head of a two-chamber carpule as described above, containing
 a bypass (3),
 an opening for receiving an intermediate plug (6) at the proximal end (4),
 a liquid-tight closure cap (5) at the distal end for piercing with an application needle, and
 an intermediate plug (6) in the opening of the proximal end.

The front chamber, which is formed in the first part-cylinder in the assembled state, contains a solid or liquid component. Preferably, the chamber contains a solid component, with particular preference a lyophilizate or powder. The rear chamber, which is formed in the second part-cylinder in the assembled state, contains a liquid component. The solid or liquid component of the front chamber and the liquid component of the rear chamber form the medicament to be administered.

The medicament contains one or more pharmaceutically active ingredients selected from the group comprising (i) a low molecular weight compound (with a molecular weight of up to 1500 Da), (ii) a peptide, (iii) a protein, (iv) DNA, (v) RNA, (vi) an antibody, (vii) an enzyme and (viii) an oligonucleotide, preferably containing at least one peptide, with preference a peptide for the treatment of Diabetes mellitus or complications of Diabetes mellitus such as for example diabetic retinopathy, with particular preference selected from the group comprising human insulin, a human insulin analog, a human insulin derivative, glucagon-like peptide-1 (GLP1), a GLP1 analog, a GLP1 derivative, exendin-3, exendin-4, an exendin-3 analog, an exendin-4 analog, an exendin-3 derivative or an exendin-4 derivative.

Insulin analogs are, for example, Gly(A21), Arg(B31), Arg (B32) human insulin; Lys (B3), Glu(B29) human insulin; Lys (B28), Pro (B29) human insulin; Asp (B28) human insulin; human insulin in which proline in the position B28 has been substituted by Asp, Lys, Leu, Val or Ala and where Lys in position B29 can be substituted by Pro; Ala (B26) human insulin; des(B28-B30) human insulin; des(B27) human insulin and des(B30) human insulin.

Insulin derivatives are, for example, B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(w-carboxyheptadecanoyl)-des(B30) human insulin and B29-N-(ω-carboxyheptadecanoyl) human insulin.

Exendin-4 preferably means exendin-4(1-39), a peptide with the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$.

Exendin-4 derivatives are, for example, selected from the following group of compounds:
H-$(Lys)_4$-des $Pro^{36}$, des $Pro^{37}$ exendin-4(1-39)-$NH_2$,
H-$(Lys)_5$-des $Pro^{36}$, des $Pro^{37}$ exendin-4(1-39)-$NH_2$,
des $Pro^{36}$ [$Asp^{28}$] exendin-4(1-39),
des $Pro^{36}$ [$IsoAsp^{28}$] exendin-4(1-39),
des $Pro^{36}$ [$Met(O)^{14}$, $Asp^{28}$] exendin-4(1-39),
des $Pro^{36}$ [$Met(O)^{14}$, $IsoAsp^{28}$] exendin-4(1-39),
des $Pro^{36}$ [$Trp(O_2)^{25}$, $Asp^{28}$] exendin-4(1-39),
des $Pro^{36}$ [$Trp(O_2)^{25}$, $IsoAsp^{28}$] exendin-4(1-39),
des $Pro^{36}$ [$Met(O)^{14}$ $Trp(O_2)^{25}$, $Asp^{28}$] exendin-4(1-39),
des $Pro^{36}$ [$Met(O)^{14}$ $Trp(O_2)^{25}$, $IsoAsp^{28}$] exendin-4(1-39); or des $Pro^{36}$ [$Asp^{28}$] exendin-4(1-39),
des $Pro^{36}$ [$IsoAsp^{28}$] exendin-4(1-39),
des $Pro^{36}$ [$Met(O)^{14}$, $Asp^{28}$] exendin-4(1-39),
des $Pro^{36}$ [$Met(O)^{14}$, $IsoAsp^{28}$] exendin-4(1-39),
des $Pro^{36}$ [$Trp(O_2)^{25}$, $Asp^{28}$] exendin-4(1-39),
des $Pro^{36}$ [$Trp(O_2)^{25}$, $IsoAsp^{28}$] Exendin-4(1-39),
des $Pro^{36}$ [$Met(O)^{14}$ $Trp(O_2)^{25}$, $Asp^{28}$] exendin-4(1-39),
des $Pro^{36}$ [$Met(O)^{14}$ $Trp(O_2)^{25}$, $IsoAsp^{28}$] exendin-4(1-39), the group -$Lys_6$-$NH_2$ being linked with the C-terminus of the exendin-4 derivative; or
an exendin-4 derivative of the sequence
H-$(Lys)_6$-des $Pro^{36}$ [$Asp^{28}$] exendin-4(1-39)-$Lys_6$-$NH_2$,
des $Asp^{28}$ $Pro^{36}$, $Pro^{37}$, $Pro^{38}$ exendin-4(1-39)-$NH_2$,
H-$(Lys)_6$-des $Pro^{36}$, $Pro^{38}$ [$Asp^{28}$] exendin-4(1-39)-$NH_2$,
H-Asn-$(Glu)_5$des $Pro^{36}$, $Pro^{37}$, $Pro^{38}$ [$Asp^{28}$] exendin-4(1-39)-$NH_2$,
des $Pro^{36}$, $Pro^{37}$, $Pro^{38}$ [$Asp^{28}$] exendin-4(1-39)-$(Lys)_6$-$NH_2$,
H-$(Lys)_6$-des $Pro^{36}$, $Pro^{37}$, $Pro^{38}$ [$Asp^{28}$] exendin-4(1-39)-$(Lys)_6$-$NH_2$,
H-Asn-$(Glu)_5$-des $Pro^{36}$, $Pro^{37}$, $Pro^{38}$ [$Asp^{28}$] exendin-4(1-39)-$(Lys)_6$-$NH_2$,
H-$(Lys)_6$-des $Pro^{36}$ [$Trp(O_2)^{25}$, $Asp^{28}$] exendin-4(1-39)-$Lys_6$-$NH_2$,
H-des $Asp^{28}$ $Pro^{36}$, $Pro^{37}$, $Pro^{38}$ [$Trp(O_2)^{25}$] exendin-4(1-39)-$NH_2$,
H-$(Lys)_6$-des $Pro^{36}$, $Pro^{37}$, $Pro^{38}$ [$TrP(O_2)^{25}$, $Asp^{28}$] exendin-4(1-39)-$NH_2$,
H-Asn-$(Glu)_5$-des $Pro^{36}$, $Pro^{37}$, $Pro^{38}$ [$Trp(O_2)^{25}$, $Asp^{28}$] exendin-4(1-39)-$NH_2$,
des $Pro^{36}$, $Pro^{37}$, $Pro^{38}$ [$Trp(O_2)^{25}$, $Asp^{28}$] exendin-4(1-39)-$(Lys)_6$-$NH_2$,
H-$(Lys)_6$-des $Pro^{36}$, $Pro^{37}$, $Pro^{38}$ [$Trp(O_2)^{25}$, $Asp^{28}$] exendin-4(1-39)-$(Lys)_6$-$NH_2$,
H-Asn-$(Glu)_5$-des $Pro^{36}$, $Pro^{37}$, $Pro^{38}$ [$Trp(O_2)^{25}$, $Asp^{28}$] exendin-4(1-39)-$(Lys)_6$-$NH_2$,
H-$(Lys)_6$-des $Pro^{36}$ [$Met(0)^{14}$, $Asp^{28}$] exendin-4(1-39)-$Lys_6$-$NH_2$,
des $Met(0)^{14}$ $Asp^{28}$ $Pro^{36}$, $Pro^{37}$, $Pro^{38}$ exendin-4(1-39)-$NH_2$,
H-$(Lys)_6$-$desPro^{36}$, $Pro^{37}$, $Pro^{38}$ [$Met(O)^{14}$, $Asp^{28}$] exendin-4(1-39)-$NH_2$,
H-Asn-$(Glu)_5$-des $Pro^{36}$, $Pro^{37}$, $Pro^{38}$ [$Met(O)^{14}$, $Asp^{28}$] exendin-4(1-39)-$NH_2$,
des $Pro^{36}$, $Pro^{37}$, $Pro^{38}$ [$Met(0)^{14}$, $Asp^{28}$] exendin-4(1-39)-$(Lys)_6$-$NH_2$,
H-$(Lys)_6$-des $Pro^{36}$, $Pro^{37}$, $Pro^{38}$ [$Met(O)^{14}$, $Asp^{28}$] exendin-4(1-39)-$(Lys)_6$-$NH_2$,
H-Asn-$(Glu)_5$ des $Pro^{36}$, $Pro^{37}$, $Pro^{38}$ [$Met(O)^{14}$, $Asp^{28}$] exendin-4(1-39)-$(Lys)_6$-$NH_2$,
H-$Lys_6$-des $Pro^{36}$ [$Met(O)^{14}$, $Trp(O_2)^{25}$, $Asp^{28}$] exendin-4(1-39)-$Lys_6$-$NH_2$,
H-des $Asp^{28}$ $Pro^{36}$, $Pro^{37}$, $Pro^{38}$ [$Met(O)^{14}$, $Trp(O_2)^{25}$] exendin-4(1-39)-$NH_2$,
H-$(Lys)_6$-des $Pro^{36}$, $Pro^{37}$, $Pro^{38}$ [$Met(O)^{14}$, $Asp^{28}$] exendin-4(1-39)-$NH_2$,
H-Asn-$(Glu)_5$-des $Pro^{36}$, $Pro^{37}$, $Pro^{38}$ [$Met(O)^{14}$, $Trp(O_2)^{25}$, $Asp^{28}$] exendin-4(1-39)-$NH_2$,
des $Pro^{36}$, $Pro^{37}$, $Pro^{38}$ [$Met(O)^{14}$, $Trp(O_2)^{25}$, $Asp^{28}$] exendin-4(1-39)-$(Lys)_6$-$NH_2$,
H-$(Lys)_6$-des $Pro^{36}$, $Pro^{37}$, $Pro^{38}$ [$Met(O)^{14}$, $Trp(O_2)^{25}$, $Asp^{28}$] exendin-4(S1-39)-$(Lys)_6$-$NH_2$,
H-Asn-$(Glu)_5$-des $Pro^{36}$, $Pro^{37}$, $Pro^{38}$ [$Met(O)^{14}$, $Trp(O_2)^{25}$, $Asp^{28}$] exendin-4(1-39)-$(Lys)_6$-$NH_2$;
or a pharmaceutically acceptable salt or solvate of exendin-4 or of one of the aforementioned exendin-4 derivatives.

The pharmaceutically active ingredient is preferably the solid component in the chamber of the front part-cylinder, with particular preference a lyophilizate or a powder.

Pharmaceutically acceptable salts are, for example, acid addition salts and basic salts. Acid addition salts are, for example, HCl or HBr addition salts. Basic salts are, for example, salts in which the cation is selected from the group of alkali salts, for example $Na^+$ or $K^+$, or the earth alkali salts, for example $Ca^{2+}$, or ammonia ions $N^+(R_1)(R_2)(R_3)(R_4)$, where $R_1$ to $R_4$ mean, independently of one another: hydrogen, $C_1$-$C_6$-alkyl, $C_2$-$C_6$-alkenyl, $C_6$-$C_{10}$-aryl, or $C_6$-$C_{10}$-heteroaryl. Further examples of pharmaceutically acceptable salts are described in "Remington's Pharmaceutical Sciences" 17. Ed. Alfonso R. Gennaro (Ed.), Mark Publishing Company, Easton, Pa., U.S.A., 1985 and in Encyclopedia of Pharmaceutical Technology.

Figure 1A:
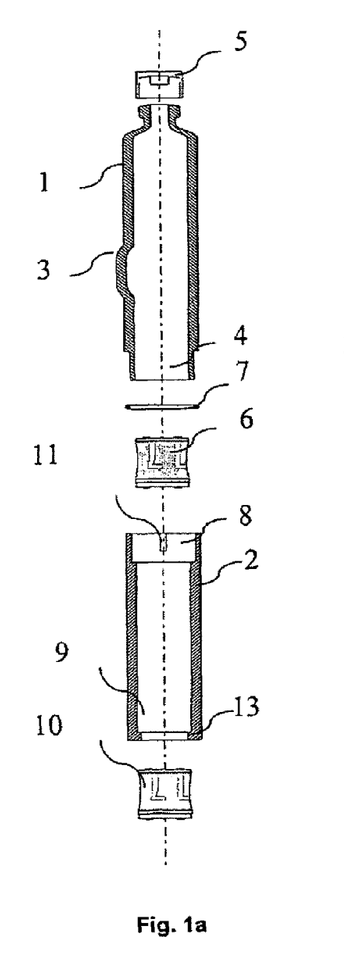
FIG. 1a shows the basic construction of the two-chamber carpule according to the invention as an exploded drawing.

In a preferred embodiment, either the proximal end (4) of the first part-cylinder, on the head side, or the distal end (8) of the second part-cylinder, on the plunger side, contains an axial groove (11) on the inner side of the receiving part-cylinder. When the two part-cylinders (1) and (2) are joined together, pressures which could press out the end plug (10) can build up in the hollow space of the part-cylinder (2). The pressure can be substantially avoided by the axial groove (11), since it can initially escape during joining together. The groove is formed in such a way that it has a length axially that is smaller than the length of the engagement of the proximal end of the one part-cylinder in the corresponding end of the other part-cylinder. Furthermore, the groove is formed in such a way that it further reduces the wall thickness of the receiving part-cylinder. If, for example, as represented in FIG. 1a, the proximal end (4) of the first part-cylinder, on the head side, engages in the distal end (8) of the second part-cylinder, on the plunger side, the pressure that is built up during joining together can initially escape through the groove (11). Only in the final assembly step is it no longer possible for the pressure to escape by way of the groove, but the pressure is so low that it can longer press out the end plug (10). In a particularly preferred embodiment, the part-cylinders (1) and (2), one of which contains an axial groove, are connected to each other by means of clamping closure.

In a further preferred embodiment, the proximal end (9) of the second part-cylinder, on the plunger side, has a stop (13). The stop prevents slipping of the end plug (10) being caused by the pressure in the direction of the proximal end produced during joining together. The stop is formed in such a way that the plunger can transfer force to the end plug through the proximal opening of the second part-cylinder.

In a further preferred embodiment, the distal end (8) of the second part-cylinder, on the plunger side, has a plug (17).

In a particularly preferred embodiment, the two-chamber carpule contains both an axial groove (11) in the receiving part-cylinder and a stop (13) at the proximal end (9) of the second part-cylinder, on the plunger side.

In an especially preferred embodiment, the two-chamber carpule contains an axial groove (11) in the receiving part of the cylinder, and a stop (13) at the proximal end (9) of the second part-cylinder, on the plunger side, and a plug at the distal end (8) of the second part-cylinder, on the plunger side.

"Proximal" means the end of a component that is facing the end plug (10) in the assembled state, that is to say facing the plunger and the thumb of the person administering the preparation when the two-chamber carpule is installed in a pen system and a plunger of the application system acting on the end plug (10) is actuated by the thumb of the person administering the preparation. The proximal end of the first part-cylinder is the end of the part cylinder that is connected to the second part-cylinder in the assembled state.

"Distal" means the end of a component that is facing the closure (5) or the outlet opening in the assembled state. For example, the distal end of the second part-cylinder is the end of the part of the cylinder that is connected to the first part-cylinder in the assembled state.

The "end on the head side of the two-chamber carpule" is the end of the two-chamber carpule that forms the head of the two-chamber carpule, that is to say comprises the closure (5) or the outlet opening.

The "end on the plunger side of the two-chamber carpule" is the end of the two-chamber carpule that comprises the end plug (10) and at which or by which the force of the plunger is transferred in a pen system.

The closure cap (5) is a device which closes the distal end of the part-cylinder (1) in a liquid- and gas-tight manner. The cap comprises a sealing element (15), for example a cartridge-like disk, and a closure element (16), for example made of aluminum or plastic, which brings about the permanent connection and the sealing force between the sealing element (15) and the part-cylinder (1). The connection may be established by methods known to a person skilled in the art, for example by crimping, flanging, pressing or screwing.

The plugs (6) (10) and (17) and the sealing element (7), independently of one another, are made of elastic material, for example rubber, preferably brominated butyl rubber, chlorinated butyl rubber or fluorinated butyl rubber. Optionally, the plugs are coated with PTFE. The plugs are preferably of a cylindrical basic form, but other basic forms corresponding to the inner form of the part-cylinders are also possible. The plugs have both a sealing function and a closing function, for example intermediate plug (6) closes and seals the proximal end (4) of the first part-cylinder. The sealing function is preferably ensured by one or more lamellar formations of the cylindrical basic form.

"Sealed" means impermeability with respect to solids, liquids, gases and with respect to germs.

Figure 1B:
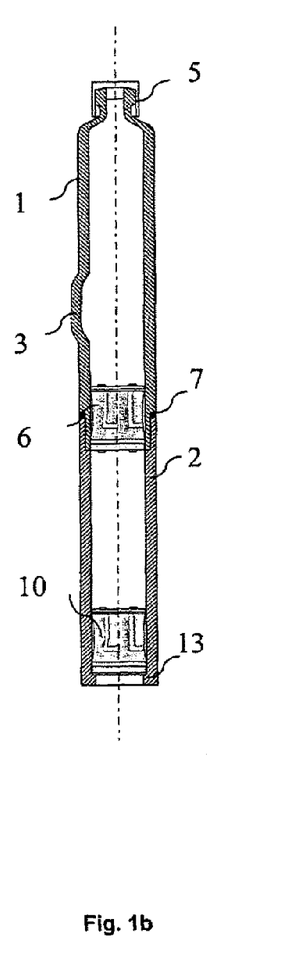
FIG. 1b shows the construction of the carpule in the assembled state.
Figure 1C:
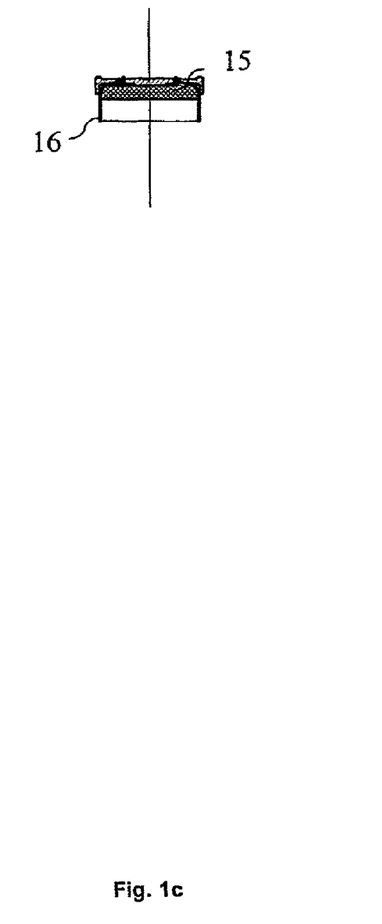
FIG. 1c shows the construction of the closure cap (5).
Figure 2A:
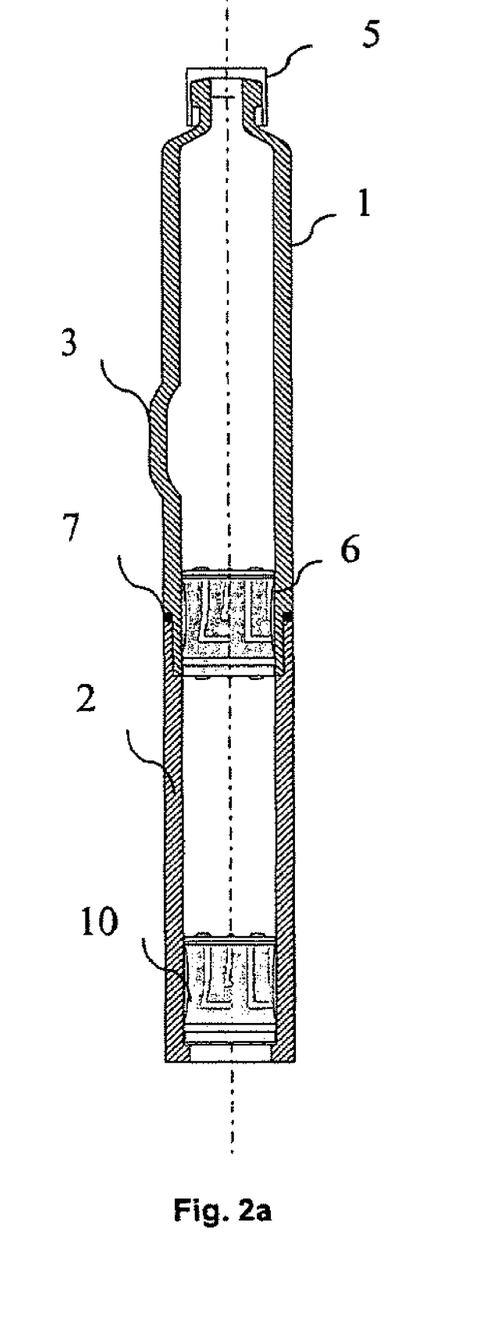
FIG. 2a shows the carpule according to the invention in comparison with a conventional two-chamber carpule in FIG. 2b.
Figure 2B:
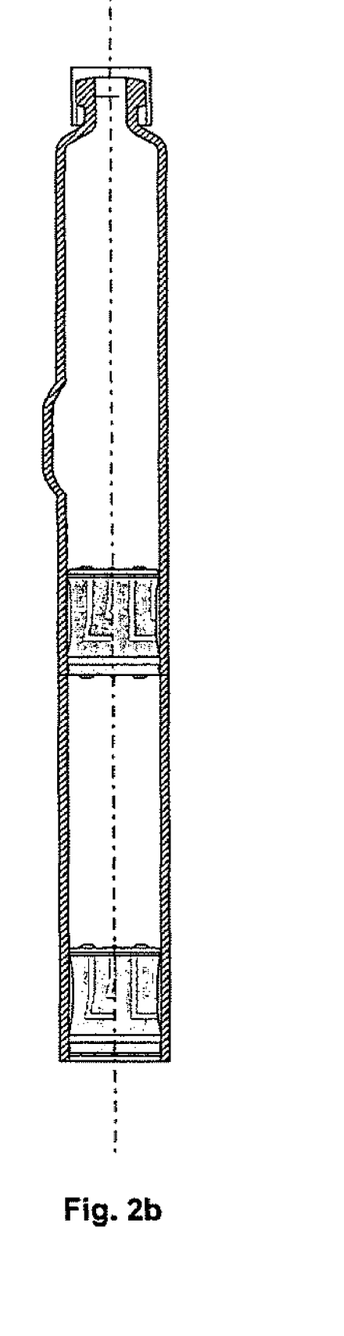

The bypass (3) is an opening which makes it possible when the two-chamber carpule is being used for a liquid component (14) to flow out of part-cylinder (2) into part-cylinder (1), bypassing the intermediate plug (6) or the intermediate plugs (6) and (17), while the medicament is administered. The bypass (3) can be created by one or more channels, which are located in the material of the wall of the part-cylinder (1), i.e. are let into or worked into the material of the wall. By appropriate forming of the material of the wall, the bypass may also be formed inward (depression running along the inner wall, not depicted) or outward (elevation widening the outer diameter, as depicted for example in FIG. 1). The arrangement may be configured axially or radially deviating from the axial direction.

The part-cylinders (1) and (2) are formed independently of each other from glass, plastic, metal or other materials, with preference transparent materials such as glass or plastic. Preferred plastics are polycarbonate, polyesters, cycloolefin copolymers (COO) or cycloolefin polymers (COP).

The first part-cylinder (1), on the head side, and the second part-cylinder (2), on the plunger side, are positively and/or nonpositively connected to each other in a way known to a person skilled in the art, for example by screw closure, plug-in closure, bayonet closure, snap-in closure or clamping closure (represented in the figures). Depending on the choice of materials, the connection is with preference self-sealing, or is for example accomplished by adhesion or welding. A sealing element (7) may optionally be used.

In one embodiment, the first part-cylinder (1), on the head side, is the receiving component. If the first part-cylinder (1), on the head side, and the second part-cylinder (2), on the plunger side, are connected to each other for example by screw closure, the first part-cylinder (1), on the head side, has an internal thread at the distal end, and the second part-cylinder (2), on the plunger side, has a corresponding external thread at the proximal end.

In a further embodiment, the second part-cylinder (2), on the plunger side, is the receiving component. If the second part-cylinder (2), on the plunger side, and the first part-cylinder (1), on the head side, are connected to each other for example by screw closure, the second part-cylinder (2), on the plunger side has an internal thread at the proximal end, and the first part-cylinder (1), on the head side, has a corresponding external thread at the distal end.

In general, a combination of all the stated general and preferred features of the embodiments is technically possible.

In a further preferred embodiment, both part-cylinders (1) and (2) consist of plastic. In a particularly preferred embodiment, the two plastic part-cylinders are connected to each other by means of a screw closure, a sealing element optionally being inserted between the part-cylinders for sealing purposes. It is especially preferred in this embodiment for the distal end (8) of the second cylinder, on the head side, to contain an axial groove (11), by way of which the pressure built up in the part-cylinder (2) during the assembly of the two part-cylinders can escape; alternatively, the end plug (10) may be positioned in the part-cylinder (2) in such a way that, during assembly, it is displaced into the desired end position by the built-up pressure. With preference, the second part-cylinder (2) contains a plug (17) at the distal end. Optionally, the part-cylinder (2) contains a stop (13) at the proximal end.

In a further preferred embodiment, the first part-cylinder (1) consists of glass and the second part-cylinder (2) consists of plastic, which part-cylinders are connected to each other with particular preference by means of a clamping closure or a plug-in closure. The sealing of the part-cylinders may take place by adhesion by means of conventional pharmaceutically acceptable adhesive, a sealing element optionally being inserted between the part-cylinders. It is especially preferred in this embodiment for the distal end (8) of the second cylinder, on the head side, to contain an axial groove (11), by way of which the pressure built up in the part-cylinder (2) during the assembly of the two part-cylinders can escape; alternatively, the end plug (10) may be positioned in the part-cylinder (2) in such a way that, during assembly, it is displaced into the desired end position by the built-up pressure. With preference, the second part-cylinder (2) contains a plug (17) at the distal end. Optionally, the part-cylinder (2) contains a stop (13) at the proximal end.

In a further preferred embodiment, both part-cylinders (1) and (2) consist of plastic, and the part-cylinders are connected to each other by way of a plug-in closure, a sealing element optionally being inserted between the part-cylinders for sealing purposes. It is especially preferred in this embodiment for the distal end (8) of the second part-cylinder, on the plunger side, to contain an axial groove (11), by way of which the pressure built up in the part-cylinder (2) during the assembly of the two part-cylinders can escape; alternatively, the end plug (10) may be positioned in the part-cylinder (2) in such a way that, during assembly, it is displaced into the desired end position by the built-up pressure. With preference, the second part-cylinder (2) contains a plug (17) at the distal end. Optionally, the part-cylinder (2) contains a stop (13) at the proximal end.

It is common to all the embodiments that the liquid component (14) and the solid component (12) are filled with preference under sterile conditions.

The two-chamber carpule according to the invention has the advantage that the two part-cylinders can be filled separately from each other through the entire diameter of the part-cylinders, and that the first part-cylinder (1), on the head side, and, if the plug (17) is present, also a second part-cylinder (2), on the plunger side, can be produced separately from each other, and consequently can be kept in storage. The second intermediate plug (17) also has the effect that there is no risk of contamination by the solid or liquid component at the points of contact between the first and second part-cylinders. The filling by way of large openings ensures a reduced likelihood of contamination of the other part-cylinder respectively, or the outside of the carpule. Since powder can be filled directly, lyophilizing is not necessary. Instead, a lyophilizate or some other solid component, preferably in powder form, can be filled in directly. The innocuous filling with powder also ensures that no influencing of the crystalline structure of the powder can occur by way of shearing forces, such as those which can occur during filling through small openings, and so influencing of the biocompatibility of the medicaments to be administered is not to be expected.

The two-chamber carpule according to the invention can be used in any application system, for example a pen system, the application system preferably including a needle for piercing a distal sealing disk (15), and a drive mechanism for moving the end plug (10) in the distal direction.

The carpule is also distinguished by outstanding cost-effectiveness, since the rapidity of filling and possibly adaptation of the rate of filling of the part-cylinder on the head side to that of the filling of the part-cylinder on the plunger side makes the method for producing and filling the carpule advantageous.

Preferably, the two part-cylinders are injection-molded under clean-room conditions, then sterilized while hermetically packed.

The use of plastic as the material for the part-cylinders additionally ensures low-cost production of the parts, the integration of functional parts required for operating a pen system on one of the part-cylinders (synergies), a simple process to establish freedom from particles, sterilization, depyrogenization, high dimensional stability and recyclability.

The invention also relates to an applicator including a two-chamber carpule as described above.

The invention also relates to a method for producing and filling two-chamber carpules, wherein a) a first part-cylinder (1), on the head side, is closed with a liquid- and gas-tight closure cap (5) at the end on the head side;
b) the chamber of the first part of the cylinder (1), on the head side, is preferably filled with solid component (12), with particular preference a powder, and closed by means of an intermediate plug (6);
c) a second part cylinder (2), on the plunger side, is closed at the proximal end with an end plug (10);
d) the chamber of a second part-cylinder (2), on the plunger side, is filled with a liquid component (14) and optionally closed with an additional intermediate plug (17); and
e) the two-part cylinders (1) and (2) are joined together, a sealing element (7) optionally being inserted between the first and second part-cylinders.

The components of the two-chamber carpule are as defined above in their general and preferred embodiments.

Alternatively, the first four steps may also be carried out in the sequence c), d), a), b).

In a preferred embodiment, the end plug (10) is positioned before the joining together of the two part-cylinders (1) and (2) in such a way that the built-up pressure displaces the plug (10) into the desired end position. The end plug (10) can in principle be introduced from both ends of the part-cylinder (2); with preference, the end plug (10) is introduced by way of the proximal end.

In a further preferred embodiment, the part-cylinders are assembled under vacuum conditions. Displacement of the end plug (10) is substantially avoided by this measure.

A person skilled in the art has at his disposal a series of known possible ways of joining together the two part-cylinders. Material-bonding (welding), nonpositively (adhesion) or positively (snap-in closure) engaging connecting techniques may be used, their suitability depending on the materials that are respectively used for the part-cylinders of the syringe. If both part-cylinders are made of plastic, a welded connection comes into consideration in particular; however, adhesion is also possible, a connecting technique that can also be used if both part-cylinders consist of glass. In a further refinement, the two cylinder parts, irrespective of whether they are produced from glass or plastic, may be connected to each other by means of a sealing snap-in connection or include a sealing element (7).

Further refinements and advantages of the invention emerge from the following description of the exemplary embodiments that are represented in the drawings.

Figure 3A:
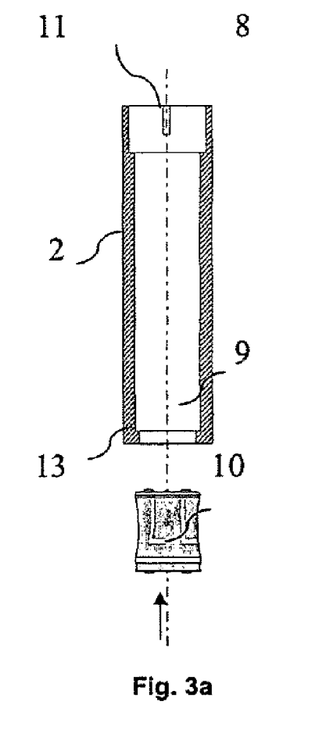
FIG. 3a and FIG. 3b shows the work being performed on the part-cylinder (2) when adding the end plug (10) and the liquid component (14).
Figure 3B:
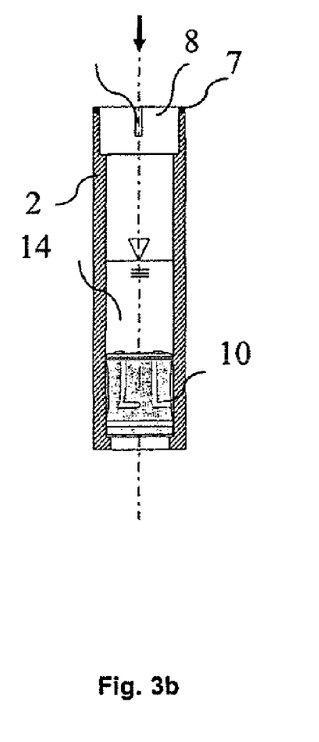
Figure 3C:
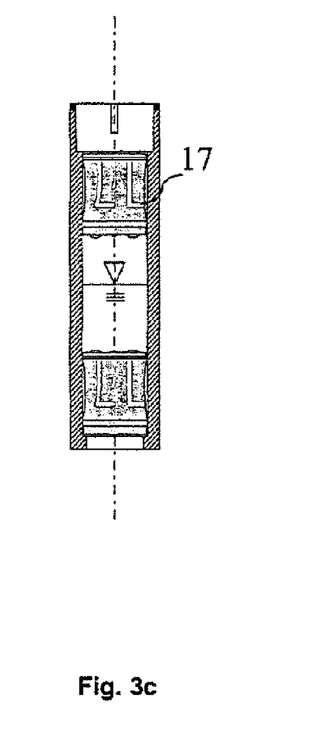
FIG. 3c shows the part-cylinder (2) being closed in a sterile manner by the fitting of an additional plug (17).
Figure 4A:
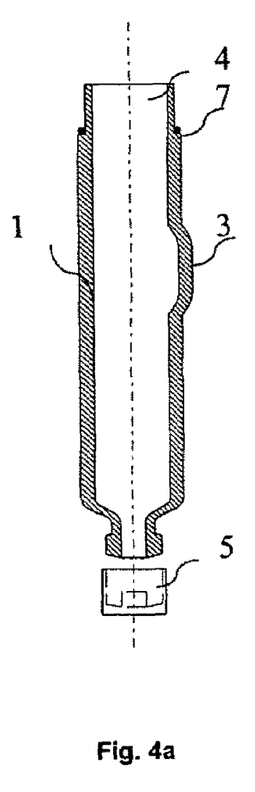
FIGS. 4a to 4d show the production and filling of the first part-cylinder (1), first the closure (5) being placed on the proximal end, a dry active preparation (12) subsequently filled in, and the intermediate plug (6) fitted.
Figure 4B:
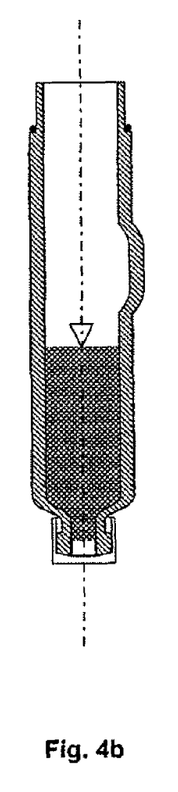
Figure 4C:
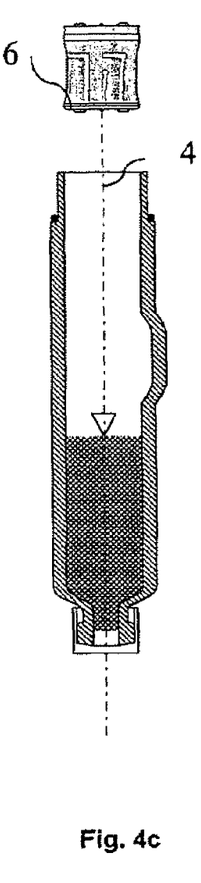
Figure 4D:
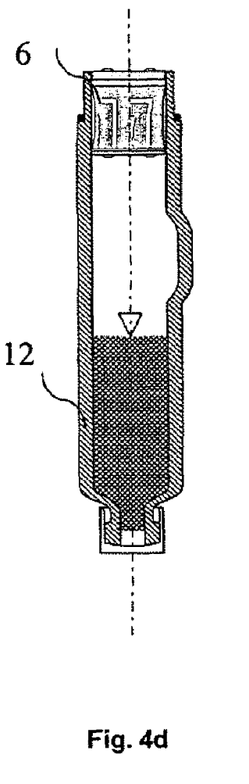
Figure 5A:
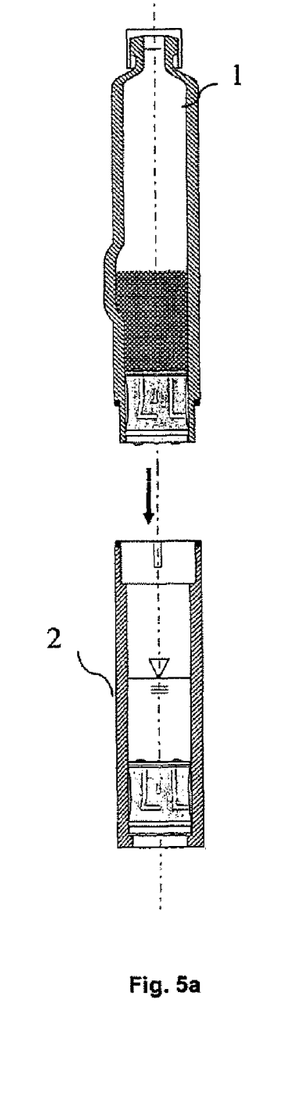
FIG. 5a represents the joining together of the two part-cylinders (1) and (2) filled with liquid carrier medium and dry active preparation.
Figure 5B:
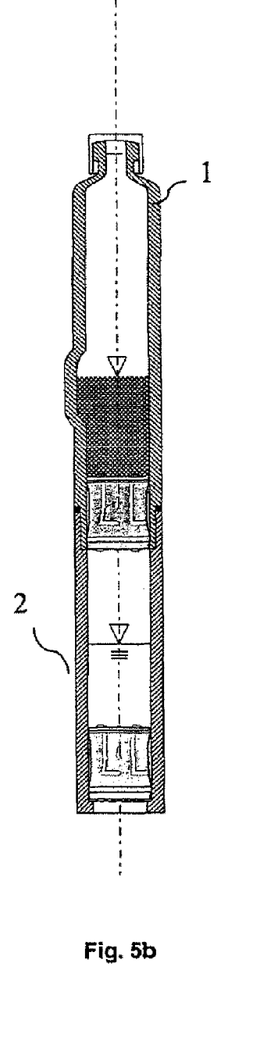
FIG. 5b shows the ready-to-use, assembled two-chamber carpule.
Figure 5C:
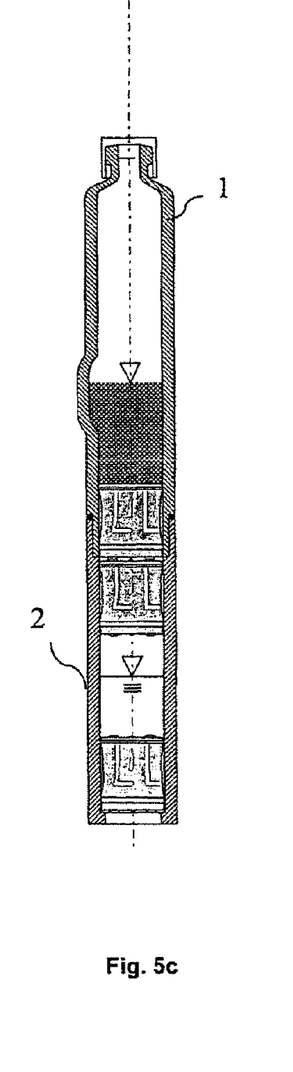
FIG. 5c shows an alternate embodiment where the second part cylinder has two end plugs.

One possible assembly procedure of the two-chamber carpule is described below (FIGS. 3-5):
1. Placing of the plug (10) into the part-cylinder (2). The end plug (10) can be introduced from both ends of the part-cylinder (2), the preferred end being the proximal end (FIG. 3a).
2. When the end plug (10) has been brought into its position, the part-cylinder (2) is filled with liquid carrier medium (14) (FIG. 3b). The length of the part-cylinder (2) is dictated by the volume of the carrier medium (14) to be filled in. Optionally, the part-cylinder (2) may be closed in a sterile manner with a plug (17).
3. The part-cylinder (1) is first closed by placing the closure cap (5) on the end on the head side (FIG. 4a). If a sealing disk (15) is used, it can be subsequently placed, or the sealing disk may be fitted on before the closure cap (5) is placed on.
4. The part-cylinder (1) is filled with a dry active preparation (12) (FIG. 4b).
5. The part-cylinder (1) on the head side is closed with the plug (6) (FIG. 4c; FIG. 4d shows the filled and closed part-cylinder (1)).
6. To complete the ready-to use two-chamber carpule, the part-cylinder (1) is pushed into the opening at the distal end (8) of the part-cylinder (2) (FIG. 5a), i.e. the part-cylinder (2) is closed by the first part-cylinder (1) (FIG. 5b).

GLOSSARY (1) first part-cylinder, on the head side
(2) second part-cylinder, on the plunger side
(3) bypass
(4) proximal end of the first part-cylinder (1), on the head side, or opening at the proximal end of the first part-cylinder (1), on the head side
(5) closure cap
(6) intermediate plug in the first part-cylinder (1), on the plunger side
(7) sealing element
(8) distal end of the second part-cylinder (2), on the plunger side, or opening at the distal end of the second part-cylinder (2), on the plunger side
(9) proximal end of the second part-cylinder (2), on the plunger side
(10) end plug
(11) axial groove
(12) solid component
(13) stop
(14) liquid component
(15) sealing disk
(16) closure element
(17) plug (intermediate plug in the second part-cylinder (2), on the plunger side)

What is claimed is:
1. A two-chamber carpule for use with a pen system comprising:
   a) a first part-cylinder having a proximal end and a distal end, on a head side, which forms a first chamber, containing a
      bypass,
      an opening for receiving an intermediate plug at the proximal end, and
      an intermediate plug in the opening of the proximal end,
   b) a liquid- and gas-tight closure at the end on the head side of the first part-cylinder, on the head side,
   c) a second part-cylinder having a proximal end and a distal end, on the head side, which fowls a second portion of the two-chamber carpule assigned to the second chamber, containing
      an opening at the distal end,
      an opening for receiving an end plug at the end on a plunger side, and
      an end plug in the opening of the end on the plunger side of the second part-cylinder,
      and optionally a second intermediate plug at the distal end;
   d) optionally a sealing element between the first part-cylinder and the second part-cylinder; and
   e) an axial groove in a receiving part-cylinder on either the proximal end of the first part-cylinder, on the head side, or on the distal end of the second part-cylinder, on the plunger side, where the axial groove is configured to allow pressure to escape when the first part-cylinder and the second part-cylinder are joined together during assembly,
wherein the first part-cylinder and second part-cylinder when in an assembled state contains a preparation and is configured to be inserted and installed into a pen system.
2. A head of a two-chamber carpule as claimed in claim 1, containing a bypass, an opening for receiving the intermediate plug at the proximal end, a liquid-tight closure cap at the distal end for piercing with an application needle, and the intermediate plug in the opening of the proximal end.

3. The two-chamber carpule as claimed in claim 1, the first and second part-cylinders and being connected to each other by means of clamping closure or plug-in closure.

4. The two-chamber carpule as claimed in claim 1, the proximal end of the second part-cylinder, on the plunger side, having a stop.

5. The two-chamber carpule as claimed in claim 1, the carpule having a stop at the proximal end of the second part-cylinder, on the plunger side, and a plug at the distal end of the second part-cylinder, on the plunger side.

6. The two-chamber carpule as claimed in claim 1, the bypass being formed as depressions running along the inner wall.

7. The two-chamber carpule as claimed in claim 1, the first and second part-cylinders and being formed independently of each other from glass, plastic or metal.

8. The two-chamber carpule as claimed in claim 1, the first and second part-cylinders and being positively and/or non-positively connected to each other.

9. The two-chamber carpule as claimed in claim 1, the medicament to be administered being a peptide for the treatment of Diabetes mellitus or complications of Diabetes mellitus.

10. The two-chamber carpule as claimed in claim 9, the peptide being exendin-4(1-39) or a peptide of the group comprising:

H-(Lys)$_4$-des Pro$^{36}$, des Pro$^{37}$ exendin-4(1-39)-NH$_2$,
H-(Lys)$_5$-des Pro$^{36}$, des Pro$^{37}$ exendin-4(1-39)-NH$_2$,
des Pro$^{36}$ [Asp$^{28}$] exendin-4(1-39),
des Pro$^{36}$ [IsoAsp$^{28}$] exendin-4(1-39),
des Pro$^{36}$ [Met(O)$^{14}$, Asp$^{28}$] exendin-4(1-39),
des Pro$^{36}$ [Met(O)$^{14}$, IsoAsp$^{28}$] exendin-4(1-39),
des Pro$^{36}$ [Trp(O$_2$)$^{25}$, Asp$^{28}$] exendin-4(1-39),
des Pro$^{36}$ [Trp(O$_2$)$^{25}$, IsoAsp$^{28}$] exendin-4(1-39),
des Pro$^{36}$ [Met(O)$^{14}$ Trp(O$_2$)$^{25}$, Asp$^{28}$] exendin-4(1-39),
des Pro$^{36}$ [Met(O)$^{14}$ Trp(O$_2$)$^{25}$, IsoAsp$^{28}$] exendin-4(1-39)
H-(Lys)$_6$-des Pro$^{36}$ [Asp$^{28}$] exendin-4(1-39)-Lys$_6$-NH$_2$,
des Asp$^{28}$ Pro$^{36}$, Pro$^{37}$, Pro38exendin-4(1-39)-NH$_2$,
H-(Lys)$_6$-des Pro$^{36}$, Pro$^{38}$ [Asp$^{28}$] exendin-4(1-39)-NH$_2$,
H-Asn-(Glu)$_5$des Pro$^{36}$, Pro$^{37}$, Pro$^{38}$ [Asp$^{28}$] exendin-4(1-39)-NH$_2$,
des Pro$^{36}$, Pro$^{37}$, Pro$^{38}$ [Asp$^{28}$] exendin-4(1-39)-(Lys)$_6$-NH$_2$,
H-(Lys)$_6$-des Pro$^{36}$, Pro$^{37}$, Pro$^{38}$ [Asp$^{28}$] exendin-4(1-39)-(Lys)$_6$-NH$_2$,
H-Asn-(Glu)$_5$-des Pro$^{36}$, Pro$^{37}$, Pro$^{38}$ [Asp$^{28}$] exendin-4(1-39)-(Lys)$_6$-NH$_2$,
H-(Lys)$_6$-des Pro$^{36}$ [TrP(O$_2$)$^{25}$, Asp$^{28}$] exendin-4(1-39)-Lys$_6$-NH$_2$,
H-des Asp$^{28}$ Pro$^{36}$, Pro$^{37}$, Pro$^{38}$ [Trp(O$_2$)$^{25}$] exendin-4(1-39)-NH$_2$,
H-(Lys)$_6$-des Pro$^{36}$, Pro$^{37}$, Pro$^{38}$ [TrP(O$_2$)$^{25}$, Asp$^{28}$] exendin-4(1-39)-NH$_2$,
H-Asn-(Glu)$_5$-des Pro$^{36}$, Pro$^{37}$, Pro$^{38}$ [Trp(O$_2$)$^{25}$, Asp$^{28}$] exendin-4(1-39)-NH$_2$,
des Pro$^{36}$, Pro$^{37}$, Pro$^{38}$ [Trp(O$_2$)$^{25}$, Asp$^{28}$] exendin-4(1-39)-(Lys)$_6$-NH$_2$,
H-(Lys)$_6$-des Pro$^{36}$, Pro$^{37}$, Pro$^{38}$ [Trp(O$_2$)$^{25}$, Asp$^{28}$] exendin-4(1-39)-(Lys)$_6$-NH$_2$,
H-Asn-(Glu)$_5$-des Pro$^{36}$, Pro$^{37}$, Pro$^{38}$ [Trp(O$_2$)$^{25}$, Asp$^{28}$] exendin-4(1-39)-(Lys)$_6$-NH$_2$,
H-(Lys)$_6$-des Pro$^{36}$ [Met(O)$^{14}$, Asp$^{28}$] exendin-4(1-39)-Lys$_6$-NH$_2$,
des Met(O)$^{14}$ Asp$^{28}$ Pro$^{36}$, Pro$^{37}$, Pro$^{38}$ exendin-4(1-39)-NH$_2$,
H-(Lys)$_6$-desPro$^{36}$, Pro$^{37}$, Pro$^{38}$ [Met(O)$^{14}$, Asp$^{28}$] exendin-4(1-39)-NH$_2$,
H-Asn-(Glu)$_5$-des Pro$^{36}$, Pro$^{37}$, Pro$^{38}$ [Met(O)$^{14}$, Asp$^{28}$] exendin-4(1-39)-NH$_2$,
des Pro$^{36}$, Pro$^{37}$, Pro$^{38}$ [Met(O)$^{14}$, Asp$^{28}$] exendin-4(1-39)-(Lys)$_6$-NH$_2$,
H-(Lys)$_6$-des Pro$^{36}$, Pro$^{37}$, Pro$^{38}$ [Met(O)$^{14}$, Asp$^{28}$] exendin-4(1-39)-(Lys)$_6$-NH$_2$,
H-Asn-(Glu)$_5$des Pro$^{36}$, Pro$^{37}$, Pro$^{38}$ [Met(O)$^{14}$, Asp$^{28}$] exendin-4(1-39)-(Lys)$_6$-NH$_2$,
H-Lys$_6$-des Pro$^{36}$ [Met(O)$^{14}$, Trp(O$_2$)$^{25}$, Asp$^{28}$] exendin-4(1-39)-Lys$_6$-NH$_2$,
H-des Asp$^{28}$ Pro$^{36}$, Pro$^{37}$, Pro$^{38}$ [Met(O)$^{14}$, Trp(O$_2$)$^{25}$] exendin-4(1-39)-NH$_2$,
H-(Lys)$_6$-des Pro$^{36}$, Pro$^{37}$, Pro$^{38}$ [Met(O)$^{14}$, Asp$^{28}$] exendin-4(1-39)-NH$_2$,
H-Asn-(Glu)$_5$-des Pro$^{36}$, Pro$^{37}$, Pro$^{38}$ [Met(O)$^{14}$, Trp(O$_2$)$^{25}$, Asp$^{28}$] exendin-4(1-39)-NH$_2$,
des Pro$^{36}$, Pro$^{37}$, Pro$^{38}$ [Met(O)$^{14}$, Trp(O$_2$)$^{25}$, Asp$^{28}$ exendin-4(1-39)-(Lys)$_6$-NH$_2$,
H-(Lys)$_6$-des Pro$^{36}$, Pro$^{37}$, Pro$^{38}$ [Met(O)$^{14}$, Trp(O$_2$)$^{25}$, Asp$^{28}$ exendin-4(S1-39)-(Lys)$_6$-NH$_2$,
H-Asn-(Glu)$_5$-des Pro$^{36}$, Pro$^{37}$, Pro$^{38}$ [Met(O)$^{14}$, Trp(O$_2$)$^{25}$, Asp$^{28}$] exendin-4(1-39)-(Lys)$_6$-NH$_2$;
or
des Pro$^{36}$ [Asp$^{28}$] exendin-4(1-39),
des Pro$^{36}$ [IsoAsp$^{28}$] exendin-4(1-39),
des Pro$^{36}$ [Met(O)$^{14}$, Asp$^{28}$] exendin-4(1-39),
des Pro$^{36}$ [Met(O)$^{14}$, IsoAsp$^{28}$] exendin-4(1-39),
des Pro$^{36}$ [Trp(O$_2$)$^{25}$, Asp$^{28}$] exendin-4(1-39),
des Pro$^{36}$ [Trp(O$_2$)$^{25}$, IsoAsp$^{28}$] Exendin-4(1-39),
des Pro$^{36}$ [Met(O)$^{14}$ Trp(O$_2$)$^{25}$, Asp$^{28}$] exendin-4(1-39),
des Pro$^{36}$ [Met(O)$^{14}$ Trp(O$_2$)$^{25}$, IsoAsp$^{28}$] exendin-4(1-39), the group -Lys$_6$-NH$_2$ being linked with the C-terminus of the exendin-4 derivative; or a pharmaceutically acceptable salt or solvate thereof.

11. An application system including a two-chamber carpule as claimed in one of claims 3 to 10.

12. A method for producing and filling a two-chamber carpule as claimed in claim 1, wherein
a) the first part-cylinder, on the head side, is closed with a liquid- and gastight closure cap at the end on the head side;
b) the chamber of the first part of the cylinder, on the head side, is preferably filled with solid component, with particular preference a powder, and closed by means of the intermediate plug;
c) the second part cylinder, on the plunger side, is closed at the proximal end with the end plug;
d) the chamber of the second part-cylinder, on the plunger side, is filled with a liquid component and optionally closed with the second intermediate plug; and
e) the two-part cylinders and are joined together, the sealing element optionally being inserted between the first and second part-cylinders.

13. The method as claimed in claim 12, wherein the end plug (10) being positioned before the joining together of the two part-cylinders and in such a way that the built-up pressure displaces the plug into the desired end position.

14. The method as claimed in claim 12, wherein the part-cylinders and being assembled under vacuum conditions.

* * * * *